United States Patent
Vakkalanka (10) Patent No.: US 10,414,773 B2
(45) Date of Patent: Sep. 17, 2019

(54) FORMS OF A PI3K DELTA SELECTIVE INHIBITOR FOR USE IN PHARMACEUTICAL FORMULATIONS

(71) Applicant: Rhizen Pharmaceuticals SA, La Chaux-de-Fonds (CH)

(72) Inventor: Swaroop K. Vakkalanka, La Chaux-de-Fonds (CH)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

(21) Appl. No.: 15/950,606

(22) Filed: Apr. 11, 2018

(65) Prior Publication Data

US 2019/0016725 A1    Jan. 17, 2019

Related U.S. Application Data

(62) Division of application No. 15/313,454, filed as application No. PCT/IB2015/053940 on May 26, 2015, now Pat. No. 9,969,740.

(30) Foreign Application Priority Data

May 27, 2014  (IN) ............................ 2596/CHE/2014
May 27, 2014  (IN) ............................ 2597/CHE/2014

(51) Int. Cl.
| | | |
|---|---|---|
| *A61K 31/519* | (2006.01) | |
| *C07D 487/04* | (2006.01) | |
| *A61K 45/06* | (2006.01) | |
| *C07C 309/30* | (2006.01) | |
| *A61P 29/00* | (2006.01) | |
| *A61P 35/00* | (2006.01) | |

(52) U.S. Cl.
CPC .......... *C07D 487/04* (2013.01); *A61K 31/519* (2013.01); *A61K 45/06* (2013.01); *A61P 29/00* (2018.01); *A61P 35/00* (2018.01); *C07C 309/30* (2013.01); *C07B 2200/13* (2013.01); *Y02A 50/422* (2018.01)

(58) Field of Classification Search
CPC ............................ A61K 31/519; C07D 487/04
USPC ........................................ 514/262.1; 544/262
See application file for complete search history.

(56) References Cited

U.S. PATENT DOCUMENTS 9,150,579 B2    10/2015  Vakkalanka et al.
9,475,818 B2    10/2016  Vakkalanka et al.

FOREIGN PATENT DOCUMENTS

WO    WO-2014006572 A1    1/2014

OTHER PUBLICATIONS

International Search Report issued in PCT/IB2015/053940 dated Aug. 4, 2015.
Byrn, et al., Pharmaceutical Solids: A Strategic Approach to Regulatory Considerations, Pharmaceutical Research, 1995, 12:7:945-954.
Noriaki Hirayama, Organic Compound Crystal Preparation Handbook— Principles and Know-how, Jul. 25, 2008, pp. 17-23, 37-40, 45-51, 57-65 (publication showing well-known technology) [No English version available].
Savjani, K.T. et al., Drug Solubility: Importance and Enhancement Techniques, International Scholarly Research Network ISRN Pharmaceutics, 2012, vol. 2012, pp. 1-10 (publication showing well-known technology).

*Primary Examiner* — Jeffrey H Murray
(74) *Attorney, Agent, or Firm* — Blank Rome LLP (57) ABSTRACT

The present invention relates to solid state forms of a p-toluenesulfonic acid salt (PTSA) of the selective PI3K delta inhibitor (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (TGR-1202). The present invention also relates to methods of preparing the same, pharmaceutical compositions containing them, and methods of treating a PI3K kinase mediated disease or disorder, such as cancer, by administering the same.

28 Claims, 4 Drawing Sheets

FORMS OF A PI3K DELTA SELECTIVE INHIBITOR FOR USE IN PHARMACEUTICAL FORMULATIONS

This application is a divisional of U.S. patent application Ser. No. 15/313,454, filed Nov. 22, 2016, which is a national stage of International Patent Application No. PCT/IB2015/053940, filed May 26, 2015, which claims the benefit of Indian Patent Application Nos. 2596/CHE/2014, filed May 27, 2014, and 2597/CHE/2014, filed May 27, 2014, each of which is hereby incorporated by reference in its entirety.

FIELD OF THE INVENTION

The present invention relates to solid state forms of a p-toluenesulfonic acid salt (PTSA) of the selective PI3K delta inhibitor (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (TGR-1202). The present invention also relates to methods of preparing the same, pharmaceutical compositions containing them, and methods of treating a PI3K kinase mediated disease or disorder, such as cancer, by administering the same.

BACKGROUND OF THE INVENTION

TGR-1202, chemically known as (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, has the following chemical structure:

The preparation of TGR-1202 and its salts is described in International Publication No. WO 2014/006572 and U.S. Patent Publication No. 2014/0011819, each of which is incorporated herein by reference in its entirety for all purposes. TGR-1202 is an investigational drug currently undergoing multiple clinical trials in the area of haematological malignancies.

WO 2014/006572 and US 2014/0011819 describe the synthesis of TGR-1202 (Example B1) and also disclose the therapeutic activity of this molecule to inhibit, regulate and/or modulate the signal transduction of PI3K.

SUMMARY OF THE INVENTION

The present invention relates to new solid state forms of a p-toluenesulfonic acid salt (PTSA) of the selective PI3K delta inhibitor (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (TGR-1202) (e.g., (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate).

The present inventors have discovered that particles of the PTSA salt of TGR-1202 having certain particle sizes exhibit enhanced solubility and pharmacokinetics upon oral administration.

In one embodiment, the PTSA salt has a d(0.9) of from about 5 to about 50 μm, such as from about 5 to about 25 μm or from about 5 to about 15 μm. The PTSA salt may also have a d(0.5) of from about 1 to about 10 μm, such as from about 2.0 to about 10 μm, from about 1 to about 5 μm, or from about 2.0 to about 5 μm. The PTSA salt may have a d(0.1) of from about 0.5 to about 1.5 μm, such as from about 0.5 to about 1.0 μm.

In another embodiment, the PTSA salt of TGR-1202 has a d(0.5) of from about 1 to about 10 μm, such as from about 2.0 to about 10 μm, from about 1 to about 5 μm, or from about 2.0 to about 5 μm. The PTSA salt may also have a d(0.1) of from about 0.5 to about 1.5 μm, such as from about 0.5 to about 1.0 μm. The PTSA salt may have a d(0.9) of from about 5 to about 50 μm, such as from about 5 to about 25 μm or from about 5 to about 15 μm.

In yet another embodiment, the PTSA salt has a d(0.1) of from about 0.5 to about 1.5 μm, such as from about 0.5 to about 1.0 μm. The PTSA salt may also have a d(0.9) of from about 5 to about 50 μm, such as from about 5 to about 25 μm or from about 5 to about 15 μm. The PTSA salt may have a d(0.9) of from about 5 to about 50 μm, such as from about 5 to about 25 μm or from about 5 to about 15 μm.

In another embodiment, the PTSA salt of TGR-1202 has a particle size distribution (PSD) where
  (i) the d(0.1) is from about 0.5 to about 1.5 μm, d(0.5) is from about 2.0 to about 10 μm and d(0.9) is from about 5.0 to about 50 μm;
  (ii) the d(0.1) is from about 0.5 to about 1.5 μm, d(0.5) is from about 2.0 to about 5.0 μm and d(0.9) is from about 5.0 to about 50 μm;
  (iii) the d(0.1) is from about 0.5 to about 1.5 μm, d(0.5) is from about 2.0 to about 10 μm and d(0.9) is from about 5.0 to about 25 μm; or
  (iv) the d(0.1) is from about 0.5 to about 1.0 μm, d(0.5) is from about 2.0 to about 5 μm and d(0.9) is from about 5.0 to about 15 μm.

In yet another embodiment, the PTSA salt of TGR-1202 has a particle size distribution (PSD) where the d(0.1) is from about 0.5 to about 1.5 μm, d(0.5) is from about 2.0 to about 10 μm and d(0.9) is from about 5.0 to about 50 μm.

In yet another embodiment, the PTSA salt of TGR-1202 has a particle size distribution (PSD) where the d(0.1) is from about 0.5 to about 1.5 μm, d(0.5) is from about 2.0 to about 5.0 μm and d(0.9) is from about 5.0 to about 50 μm.

In yet another embodiment, the PTSA salt of TGR-1202 has a particle size distribution (PSD) where the d(0.1) is from about 0.5 to about 1.0 μm, d(0.5) is from about 2.0 to about 10.0 μm and d(0.9) is from about 5.0 to about 15 μm.

In yet another embodiment, the PTSA salt of TGR-1202 has a particle size distribution (PSD) where the d(0.1) is from about 0.5 to about 1.0 μm, d(0.5) is from about 2.0 to about 5.0 μm and d(0.9) is from about 5.0 to about 15 μm.

In yet another embodiment, at most 5%, at most 3%, at most 2%, or at most 1% of the particles of the PTSA salt of TGR-1202 have a particle size less than 1.0 microns. At the same time, at least 95%, at least 96%, at least 97%, at least 98%, at least 99%, or at least 99.5% of the particles of the PTSA salt of TGR-1202 have a particle size less than 100 microns. In one particular embodiment, the PTSA salt of TGR-1202 also has a d(0.1) of from about 0.5 to about 1.5 μm, d(0.5) of from about 2.0 to about 10 μm and d(0.9) of from about 5.0 to about 50 μm. In another embodiment, the PTSA salt of TGR-1202 also has a d(0.1) of from about 0.5 to about 1.5 μm, d(0.5) of from about 2.0 to about 5.0 μm and d(0.9) of from about 5.0 to about 50 μm. In yet another embodiment, the PTSA salt of TGR-1202 also has a d(0.1) of from about 0.5 to about 1.5 μm, d(0.5) of from about 2.0 to about 10 μm and d(0.9) of from about 5.0 to about 25 μm. In yet another embodiment, the PTSA salt of TGR-1202 has a d(0.1) of from about 0.5 to about 1.0 μm, d(0.5) of from about 2.0 to about 5.0 μm and d(0.9) of from about 5.0 to about 15 μm.

In yet another embodiment, at most 5%, at most 3%, at most 2%, or at most 1% of the particles of the PTSA salt of TGR-1202 have a particle size less than 1.0 microns. At the same time, at least 95%, at least 96%, at least 97%, at least 98%, at least 99%, or at least 99.5% of the particles of the PTSA salt of TGR-1202 have a particle size less than 50 microns. In one particular embodiment, the PTSA salt of TGR-1202 also has a d(0.1) of from about 0.5 to about 1.5 μm, d(0.5) of from about 2.0 to about 10 μm and d(0.9) of from about 5.0 to about 50 μm. In another embodiment, the PTSA salt of TGR-1202 also has a d(0.1) of from about 0.5 to about 1.5 μm, d(0.5) of from about 2.0 to about 5.0 μm and d(0.9) of from about 5.0 to about 50 μm. In yet another embodiment, the PTSA salt of TGR-1202 also has a d(0.1) of from about 0.5 to about 1.5 μm, d(0.5) of from about 2.0 to about 10 μm and d(0.9) of from about 5.0 to about 25 μm. In yet another embodiment, the PTSA salt of TGR-1202 has a d(0.1) of from about 0.5 to about 1.0 μm, d(0.5) of from about 2.0 to about 5.0 μm and d(0.9) of from about 5.0 to about 15 μm.

In yet another embodiment, at most 5%, at most 3%, at most 2%, or at most 1% of the particles of the PTSA salt of TGR-1202 have a particle size less than 1.0 microns. At the same time, at least 95%, at least 96%, at least 97%, at least 98%, at least 99%, or at least 99.5% of the particles of the PTSA salt of TGR-1202 have a particle size less than 25 microns. In one particular embodiment, the PTSA salt of TGR-1202 also has a d(0.1) of from about 0.5 to about 1.5 μm, d(0.5) of from about 2.0 to about 10 μm and d(0.9) of from about 5.0 to about 25 μm. In yet another embodiment, the PTSA salt of TGR-1202 has a d(0.1) of from about 0.5 to about 1.0 μm, d(0.5) of from about 2.0 to about 5.0 μm and d(0.9) of from about 5.0 to about 15 μm.

In yet another embodiment, at most 5%, at most 3%, at most 2%, or at most 1% of the particles of the PTSA salt of TGR-1202 have a particle size less than 1.0 microns. At the same time, at least 95%, at least 96%, at least 97%, at least 98%, at least 99%, or at least 99.5% of the particles of the PTSA salt of TGR-1202 have a particle size less than 15 microns. In one particular embodiment, the PTSA salt of TGR-1202 also has a d(0.1) of from about 0.5 to about 1.5 μm, d(0.5) of from about 2.0 to about 10 μm and d(0.9) of from about 5.0 to about 25 μm. In yet another embodiment, the PTSA salt of TGR-1202 has a d(0.1) of from about 0.5 to about 1.0 μm, d(0.5) of from about 2.0 to about 5.0 μm and d(0.9) of from about 5.0 to about 15 μm.

Figure 1:
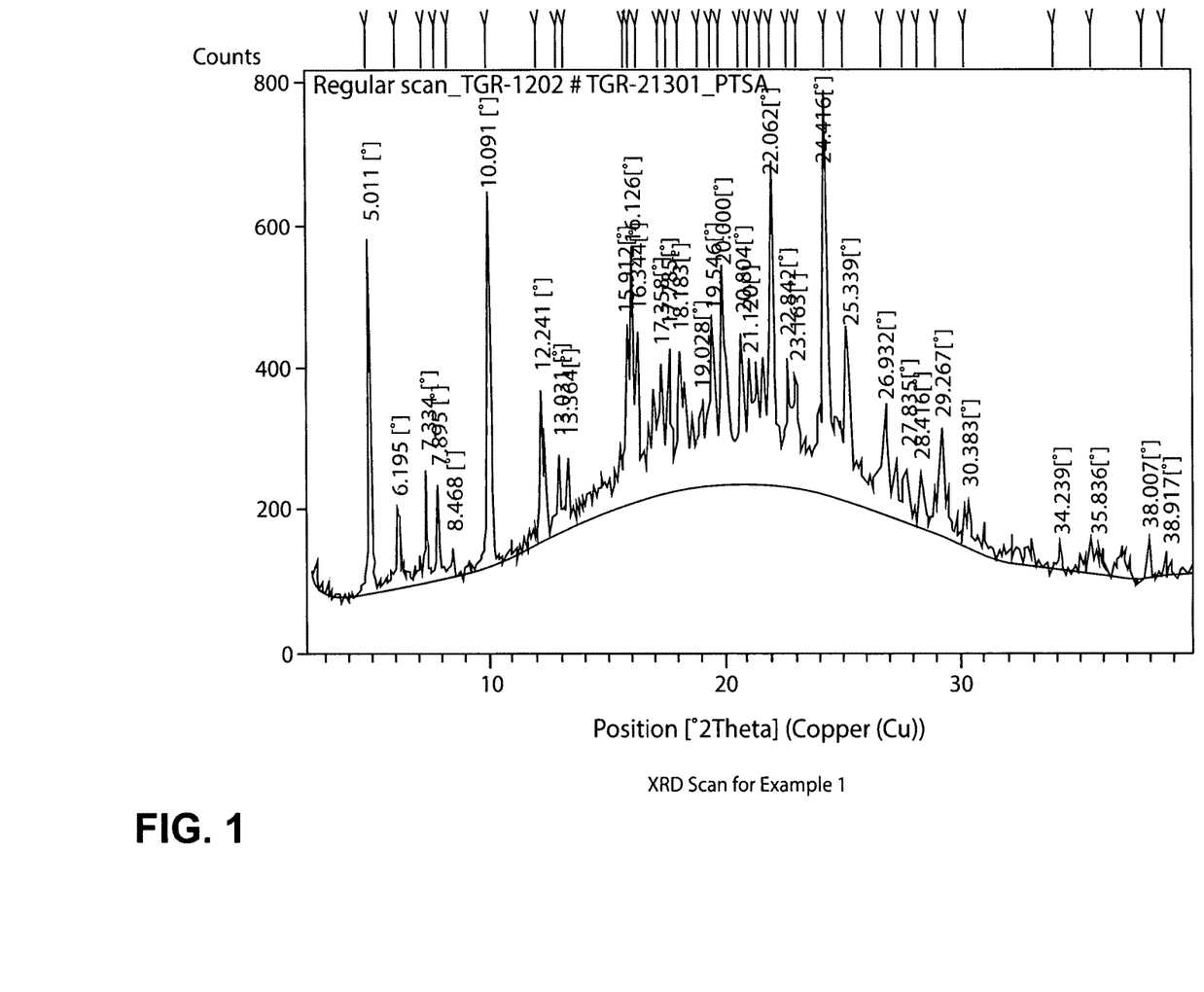
FIG. 1 is an XRPD spectrum for the PTSA salt of TGR-1202 prepared by the process described in Example 1 (Form A).

In yet another embodiment, the PTSA salt of TGR-1202 exhibits an X-ray powder diffraction (XRPD) pattern substantially as shown in FIG. 1 (hereinafter referred to as Form A).

In yet another embodiment, the PTSA salt of TGR-1202 exhibits a differential scanning calorimeter (DSC) pattern having a characteristic endothermic peak at about 154° C. (Form A).

In yet another embodiment, the PTSA salt of TGR-1202 exhibits an XRPD pattern exhibiting one or more peaks selected from 5.0, 10.1, 15.9, 16.1, 16.3, 20.0, 22.1, and 24.4±0.05, 0.1, or 0.2° 2Θ. For example, the salt may exhibit an XRPD pattern having one or more peaks (such as 2, 3, 4, 5, 6, 7 or 8 peaks) selected from 5.01, 10.09, 15.91, 16.13, 16.34, 20.00, 22.06 and 24.42±0.05, 0.1, or 0.2° 2Θ.

Figure 2:
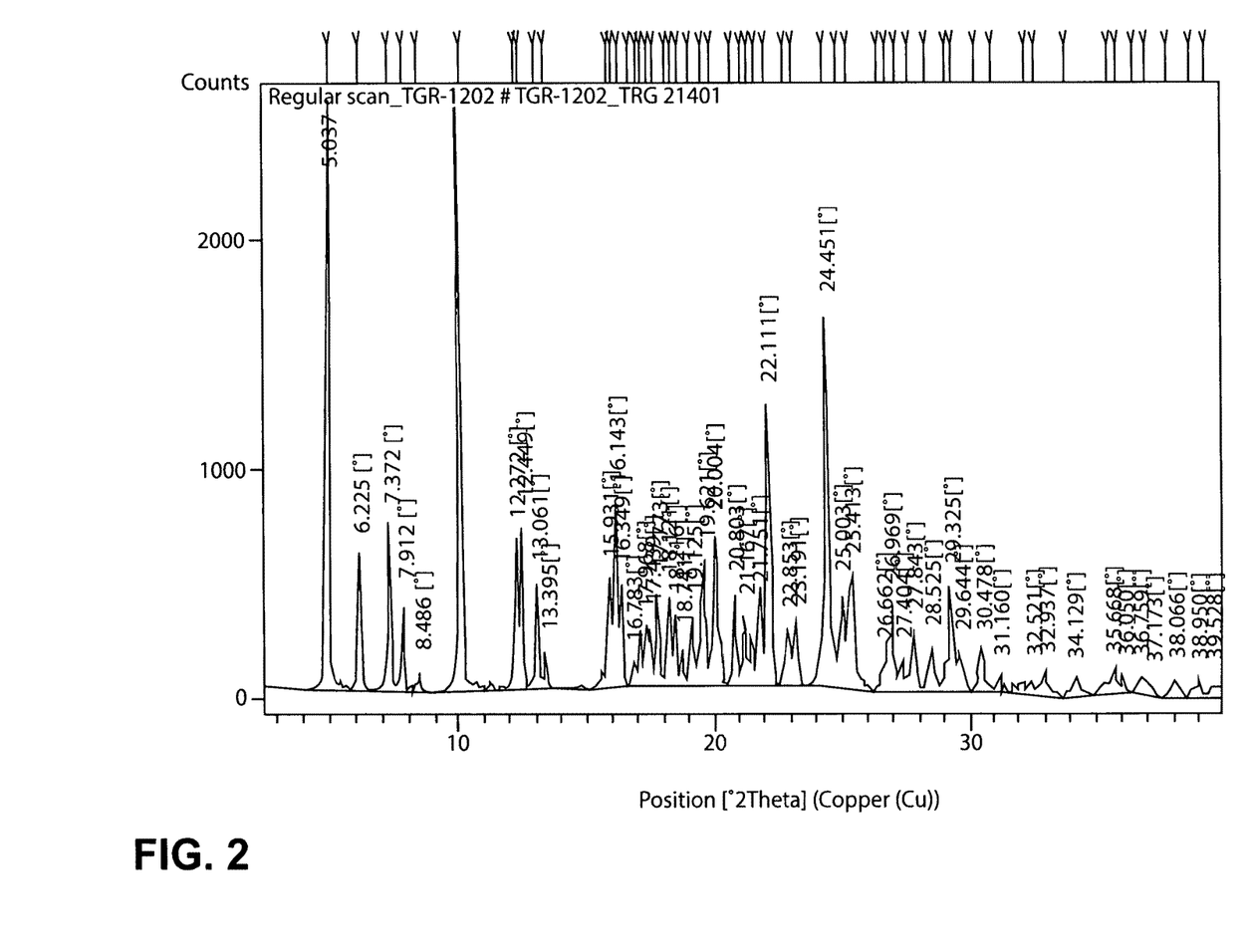
FIG. 2 is an XRPD spectrum for the PTSA salt of TGR-1202 prepared by the process described in Example 2 (Form B).
Figure 3:
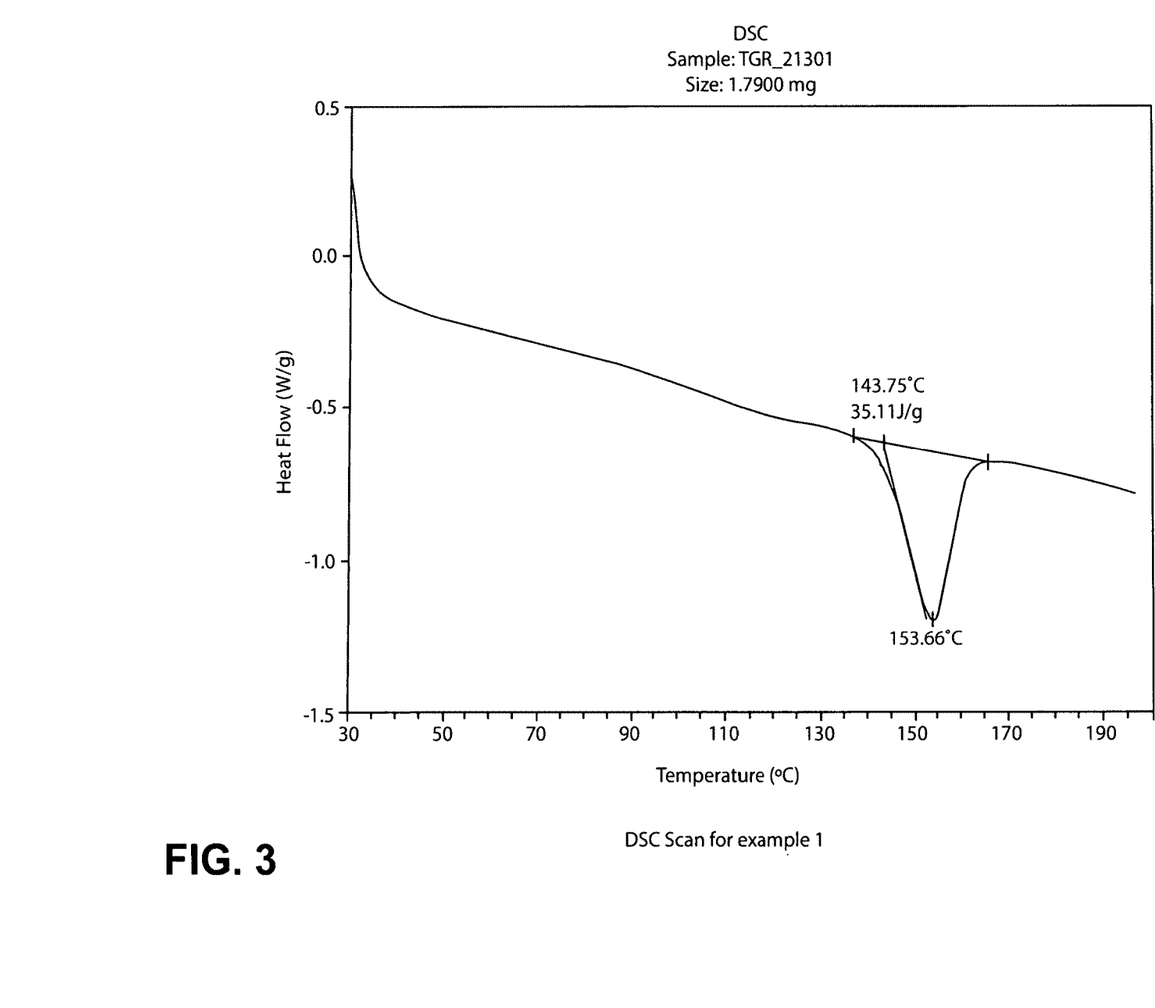
FIG. 3 is a DSC trace for the PTSA salt of TGR-1202 prepared by the process described in Example 1 (Form A).
Figure 4:
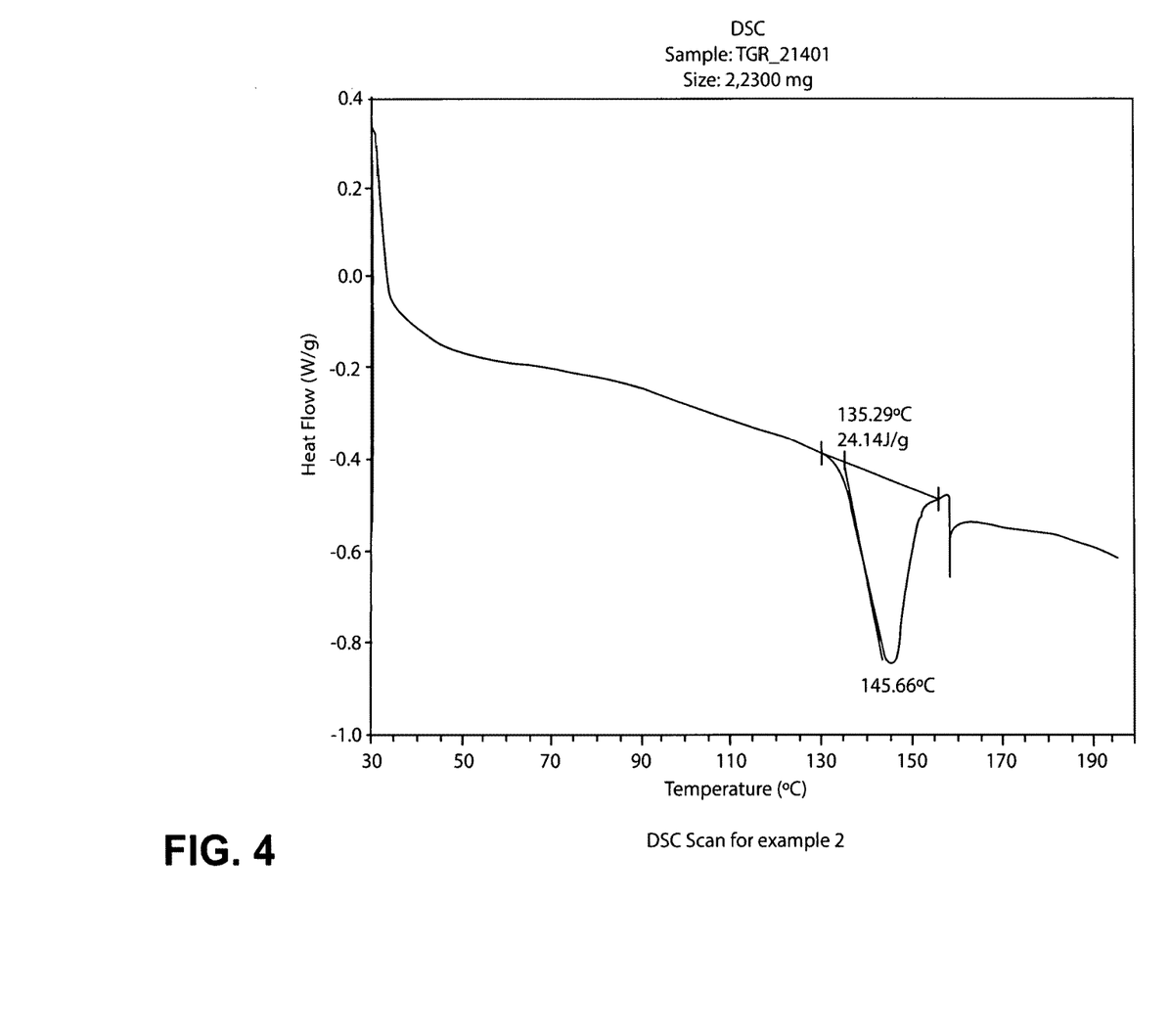
FIG. 4 is a DSC trace for the PTSA salt of TGR-1202 prepared by the process described in Example 2 (Form B).

In yet another embodiment, the PTSA salt of TGR-1202 exhibits an XRPD pattern substantially as shown in FIG. 2 (hereinafter referred to as Form B).

In yet another embodiment, the PTSA salt of TGR-1202 exhibits a differential scanning calorimeter (DSC) pattern having a characteristic endothermic peak at about 146° C. (Form B).

In yet another embodiment, the PTSA salt of TGR-1202 exhibits an XRPD pattern having one or more peaks selected from 5.0, 10.1, 22.1, and 24.5±0.05, 0.1, or 0.2° 2Θ. For example, the salt may exhibit an XRPD pattern having one or more peaks selected from 5.04, 10.13, 22.11 and 24.45±0.05, 0.1, or 0.2° 2Θ.

Yet another embodiment is crystalline Form B of a PTSA salt of TGR-1202 having a particle size distribution (PSD) which is defined by a d(0.1) of from about 0.5 to about 1.5 μm, d(0.5) of from about 2.0 to 10 μm and d(0.9) of from about 5 to about 50 μm.

Yet another embodiment is crystalline Form B of a PTSA salt of TGR-1202 having a particle size distribution (PSD) which is defined by a d(0.1) of from about 0.5 to about 1.5 μm, d(0.5) of from about 2.0 to about 5 μm and d(0.9) of from about 5 to about 25 μm.

Yet another embodiment is crystalline Form B of a PTSA salt of TGR-1202 having a particle size distribution (PSD) which is defined by a d(0.1) of from about 0.5 to about 1.0 μm, d(0.5) of from about 2.0 to about 5 μm and d(0.9) of from about 5 to about 15 μm.

The present invention further provides a pharmaceutical composition comprising a PTSA salt of TGR-1202 according to any of the embodiments described herein (e.g., having a particle size distribution as defined by any embodiment herein) and a pharmaceutically acceptable excipient.

The present invention further provides a pharmaceutical composition comprising crystalline Form B of a PTSA salt of TGR-1202 as described in any embodiment herein and a pharmaceutically acceptable excipient.

The present invention further provides a pharmaceutical composition comprising crystalline Form B of a PTSA salt of TGR-1202 having a particle size distribution as defined in any embodiment herein and a pharmaceutically acceptable excipient.

Another embodiment is a PTSA salt of TGR-1202 having an XRPD pattern substantially as shown in FIG. 2, suitable for use in a pharmaceutical composition for the treatment of a PI3K associated disease, disorder or condition, e.g., a proliferative disease such as cancer.

Another embodiment is a PTSA salt of TGR-1202 having a particle size distribution as defined in any embodiment herein, suitable for use in a pharmaceutical composition for the treatment of a PI3K associated disease, disorder or condition, e.g., a proliferative disease such as cancer.

The present invention further provides a pharmaceutical composition comprising crystalline Form B of a PTSA salt of TGR-1202 having a particle size distribution as defined in any embodiment herein and a pharmaceutically acceptable excipient. The pharmaceutical composition may further comprise one or more of additional active ingredients, such as other active agents (such as anti-cancer agents and the active agents discussed below).

The invention further provides a pharmaceutical composition comprising a PTSA salt of TGR-1202 having a particle size distribution as defined in any embodiment herein and a pharmaceutically acceptable excipient. The pharmaceutical composition may further comprise one or more of additional active ingredients, such as other active agents (such as anti-cancer agents and the active agents discussed below).

One embodiment is a solid oral pharmaceutical composition (such as a tablet) comprising a PTSA salt of TGR-1202 as described herein and one or more solubilizers (such as hydroxypropyl betadex). The weight ratio of PTSA salt to solubilizer (such as hydroxypropyl betadex) can range from about 1.5:1 to about 1:1.5. The composition may further include one or more excipients selected from suspending agents (such as hydroxypropyl cellulose), dispersing agents (such as microcrystalline cellulose), disintegrants (such as croscarmellose sodium), lubricants (such as magnesium stearate), and any combination of any of the foregoing.

In additional embodiments, the PTSA salt as defined in any embodiment herein has an enantiomeric excess (e.g.,) of at least about 60%, at least about 75%, at least about 80%, at least about 85%, at least about 90%, at least about 95%, at least about 98%, at least about 99%, at least about 99.5% or at least about 99.9%.

Yet another embodiment is a crystalline PTSA salt of TGR-1202, wherein (i) the crystalline salt exhibits an XRPD pattern having one or more peaks (such as 2, 3 or 4 peaks) selected from 5.0, 10.1, 22.1, and 24.5±0.2° 2Θ and (ii) the crystalline salt is substantially free of other solid state forms of the PTSA salt.

Yet another embodiment is a crystalline PTSA salt of TGR-1202, wherein (i) the crystalline salt exhibits an XRPD pattern having one or more peaks (such as 2, 3 or 4 peaks) selected from 5.0, 10.1, 22.1, and 24.5±0.2° 2Θ and (ii) the crystalline salt contains less than 5% (such as less than 4%, less than 3%, less than 2% or less than 1%) of other solid state forms of the PTSA salt.

In another aspect, the present invention relates to a method of preparing a crystalline PTSA salt of TGR-1202 (i.e., a p-toluenesulfonic acid salt of (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one). In one embodiment, the method comprises removing the solvent from a mixture of a PTSA salt of TGR-1202 and an ether solvent, such as di-tert-butyl ether, diethyl ether, diethylene glycol diethyl ether, diisopropyl ether, dimethoxyethane, dimethoxymethane, ethyl tert-butyl ether, methoxyethane, 2-(2-methoxyethoxy)ethanol, methyl tert-butyl ether, 2-methyltetrahydrofuran, tetrahydrofuran and tetrahydropyran. The mixture is preferably stirred (for example, for 3, 6, 12, or more hours) prior to removing the solvent. The solvent may be removed by drying. In one preferred embodiment, the method comprises stirring, filtering and drying a mixture of a PTSA salt of TGR-1202 and an ether solvent. The mixture is preferably a suspension, which can, for example, be formed by suspending a PTSA salt of TGR-1202 in an ether solvent.

In another aspect, the present invention is directed to a method of inhibiting PI3K delta in a patient in need thereof by administering to the patient an effective amount of a PTSA salt of TGR-1202 as described herein (e.g., crystalline Form B of the PTSA salt of TGR-1202) and having a particle size distribution as defined in any embodiment herein).

Yet another embodiment is a method of treating, preventing, and/or inhibiting a PI3K protein kinase mediated disease, disorder or condition (such as cancer or other proliferative disease or disorder) in a patient by administering to the patient an effective amount of a PTSA salt of TGR-1202 as described herein (e.g., crystalline Form B of the PTSA salt of TGR-1202).

Yet another embodiment is a method of treating a PI3K associated disease, disorder or condition in a patient by administering to the patient an effective amount of a PTSA salt of TGR-1202 as described herein (e.g., crystalline Form B of the PTSA salt of TGR-1202). In one embodiment, the amount of the crystalline form B of the PTSA salt of TGR-1202 administered is sufficient to treat a PI3K associated disease, disorder or condition by inhibition of PI3K delta.

Yet another embodiment of the present invention is a method for treating a proliferative disease by administering to a patient in need of such treatment an effective amount of a PTSA salt of TGR-1202 as described herein (e.g., crystalline Form B of the PTSA salt of TGR-1202). In one embodiment, the amount of crystalline form B of the PTSA salt of TGR-1202 administered is sufficient to treat the proliferative disease by inhibition of PI3K delta.

Yet another embodiment of the present invention is a method for treating a proliferative disease by administering to a patient in need of such treatment an effective amount of a PTSA salt of TGR-1202 as described herein (e.g., crystalline Form B of the PTSA salt of TGR-1202), in combination (simultaneously or sequentially) with at least one other anti-cancer agent. In one embodiment, the amount of PTSA salt of TGR-1202 (e.g., Form B of the PTSA salt of TGR-1202) administered is sufficient to treat (or facilitate treatment of) the proliferative disease by inhibition of PI3K delta.

Yet another embodiment is a method of treating a PI3K associated disease, disorder or condition in a patient, comprising administering to a patient in need of such treatment an effective amount of a PTSA salt of TGR-1202 as described herein (e.g., crystalline Form B of PTSA salt of TGR-1202), optionally admixed with at least one pharmaceutically acceptable excipients. In particular embodiments, the composition comprises a therapeutically effective amount of crystalline Form B of the PTSA salt of TGR-1202 according to any embodiment herein (e.g., a crystalline Form B of the PTSA salt of TGR-1202 having a particle size distribution as defined in any embodiment herein) for the treatment of a PI3K associated disease, disorder or condition.

Specific embodiments provide a method of treating cancer in a patient, comprising administering to the patient a pharmaceutical composition comprising a PTSA salt of TGR-1202 as described herein (e.g., crystalline Form B of PTSA salt of TGR-1202), optionally admixed with at least one pharmaceutically acceptable excipient. In particular embodiments, the composition comprises of a therapeutically effective amount of crystalline Form B of PTSA salt of TGR-1202 according to any embodiment herein (e.g., a crystalline Form B of PTSA salt of TGR-1202 having a particle size distribution as defined in any embodiment herein) for the treatment of cancer in a patient.

The crystalline Form B of PTSA salt of TGR-1202 according to any embodiment herein (e.g., a crystalline Form B of PTSA salt of TGR-1202 having a particle size distribution as defined in any embodiment herein) is useful in the treatment of a variety of cancers, including, but not limited to, the following:

carcinoma, including that of the bladder, breast, colon, kidney, liver, lung (including small cell lung cancer), oesophagus, gall bladder, uterus, ovary, testes, larynx, oral cavity, gastrointestinal tract (e.g., oesophagus, stomach, pancreas), brain, cervix, thyroid, prostate, blood, and skin (including squamous cell carcinoma);

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The PTSA salt of TGR-1202 described herein (including the crystalline Form B) as modulators of apoptosis are useful in the treatment, prevention, and inhibition of cancer (including, but not limited to, those types mentioned herein).

The PTSA salt of TGR-1202 described herein (including the crystalline Form B) are useful in the chemoprevention of cancer. Chemoprevention involves inhibiting the development of invasive cancer by blocking the initiating mutagenic event, blocking the progression of pre-malignant cells that have already suffered an insult, or inhibiting tumor relapse. The PTSA salt, including Form B of it, is also useful in inhibiting tumor angiogenesis and metastasis. One embodiment of the invention is a method of inhibiting tumor angiogenesis or metastasis in a patient by administering an effective amount of a PTSA salt of TGR-1202 (such as crystalline Form B of PTSA salt of TGR-1202).

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering an effective amount of one or more compounds of the present invention.

Examples of immune disorders which can be treated by the compounds of the present invention include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, idiopathic pulmonary fibrosis (IPF) (or cryptogenic fibrosing alveolitis (CFA) or idiopathic fibrosing interstitial pneumonia), pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Yet another embodiment is a method of treating leukemia in a patient by administering a therapeutically effective amount of a compound of the present invention. For example, the compounds of the present invention are effective for treating chronic lymphocytic leukemia (CLL), non-Hodgkin lymphoma (NHL), acute myeloid leukemia (AML), multiple myeloma (MM), small lymphocytic lymphoma (SLL), and indolent non-Hodgkin's lymphoma (I-NHL).

In the aforementioned methods of treatment, one or more additional active agents can be administered with a PTSA salt of TGR-1202, such as the crystalline form B of PTSA salt of TGR-1202 as described in any embodiment herein. For example, the PTSA salt of TGR-1202 as described in any embodiment herein is useful in combination (administered together or sequentially) with known anti-cancer treatments such as chemotherapy, radiation therapy, biological therapy, bone marrow transplantation, stem cell transplant or any other anticancer therapy or with one or more cytostatic, cytotoxic or anticancer agents or targeted therapy either alone or in combination, such as but not limited to, for example, DNA interactive agents, such as fludarabine, cisplatin, chlorambucil, bendamustine or doxorubicin; alkylating agents, such as cyclophosphamide; topoisomerase II inhibitors, such as etoposide; topoisomerase I inhibitors, such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); CD20 monoclonal antibodies such as rituximab, ublixtumab (TGR-1101), ofatumumab (HuMax; Intracel), ocrelizumab, veltuzumab, GA101 (obinutuzumab), AME-133v (LY2469298, Applied Molecular Evolution), ocaratuzumab (Mentrik Biotech), PRO131921, tositumomab, hA20 (Immunomedics, Inc.), ibritumomab-tiuxetan, BLX-301 (Biolex Therapeutics), Reditux (Dr. Reddy's Laboratories), and PRO70769 (described in WO2004/056312); other B-cell targeting monoclonal antibodies such as belimumab, atacicept or fusion proteins such as blisibimod and BR3-Fc; other monoclonal antibodies such as alemtuzumab; CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP-CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, adriamycin, cyclophosphamide, etoposide); and other protein kinase modulators.

The crystalline form B of PTSA salt of TGR-1202 as described in any embodiment herein is also useful in combination (administered together or sequentially) with one or more steroidal anti-inflammatory drugs, non-steroidal anti-inflammatory drugs (NSAIDs) or immune selective anti-inflammatory derivatives (ImSAIDs).

DETAILED DESCRIPTION OF THE INVENTION

As used herein the following definitions shall apply unless otherwise indicated.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; and AIDS=Acquired Immuno Deficiency Syndrome.

Abbreviations used herein have their conventional meaning within the chemical and biological arts, unless otherwise indicated.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including, but not limited to, disease treatment. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications. In some embodiments, the patient is a mammal, and in some embodiments, the patient is human. For veterinary purposes, the term "subject" and "patient" include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

"Radiation therapy" refers to exposing a patient, using methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including without limitation x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

As used herein, the terms "PI3-kinase delta selective inhibitor" and "PI3-kinase δ selective inhibitor" generally refer to a compound that inhibits the activity of the PI3- kinase δ isozyme more effectively than other isozymes of the PI3K family (alpha, beta, and gamma). For instance, the PI3-kinase δ selective inhibitor may refer to a compound that exhibits a 50% inhibitory concentration (IC50) with respect to the delta type I PI3-kinase that is at least 10-fold, at least 20-fold, at least 50-fold, at least 100-fold, or lower, than the inhibitor's IC50 with respect to the rest of the other type I PI3-kinases (i.e., alpha, beta, and gamma).

Inhibition of PI3-kinase δ may be of therapeutic benefit in treatment of various conditions, e.g., conditions characterized by an inflammatory response including but not limited to autoimmune diseases, allergic diseases, and arthritic diseases. Importantly, inhibition of PI3-kinase δ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis Inflammatory responses may result from infection with pathogenic organisms and viruses, noninfectious means such as trauma or reperfusion following myocardial infarction or stroke, immune responses to foreign antigens, and autoimmune diseases Inflammatory responses amenable to treatment with the methods and compounds according to the invention encompass conditions associated with reactions of the specific defense system as well as conditions associated with reactions of the non-specific defense system.

The therapeutic methods of the invention include methods for the treatment of conditions associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers to an immune response directed against grafted tissue (including organs or cells (e.g., bone marrow), characterized by a loss of function of the grafted and surrounding tissues, pain, swelling, leukocytosis, and thrombocytopenia).

"Allergic disease" as used herein refers to any symptoms, tissue damage, or loss of tissue function resulting from allergy.

"Arthritic disease" as used herein refers to any disease that is characterized by inflammatory lesions of the joints attributable to a variety of etiologies.

"Dermatitis" as used herein refers to any of a large family of diseases of the skin that are characterized by inflammation of the skin attributable to a variety of etiologies.

The term "particle size distribution" of a powder, or granular material, or particles dispersed in fluid, as used herein, is a list of values or a mathematical function that defines the relative amounts of particles present, sorted according to size. The d(0.1), d(0.5) and d(0.9) values indicate that 10%, 50% and 90% of the particles measured were less than or equal to the size stated. For example, values of d(0.1)=3, d(0.5)=10 and d(0.9)=100 mean that 10% of the particles were less than or equal to 3 μm, 50% were less than or equal to 10 μm and 90% were less than or equal to 100 μm.

The terms d(0.1), d(0.5), and d(0.9) refer to the mesh size of a single notional sieve allowing 10%, 50%, or 90% of the total of all particles of the sample to pass. Thus d(0.1)=2-100 μm indicates that the upper limit of the particle size range defining the 10% of the smallest particles in the sample is between 2 μm to 100 μm. Thus 10% of the total particles have a particle size of not more than the d(0.1) value meaning in this case that they have a maximum size of 2 μm to 100 μm.

Pharmaceutical Compositions

The present invention provides a pharmaceutical composition comprising a PTSA salt of TGR-1202 as described herein and one or more pharmaceutically acceptable excipients. For example, the PTSA salt of TGR-1202 may have the particle size distribution described herein and/or crystalline properties described herein.

In one aspect, the present invention provides a pharmaceutical composition comprising crystalline Form B of PTSA salt of TGR-1202 according to any embodiment herein (e.g., a crystalline Form B of PTSA salt of TGR-1202 having a particle size distribution as defined in any embodiment herein) and one or more pharmaceutically acceptable excipients. In one embodiment, the pharmaceutical composition includes a therapeutically effective amount of crystalline Form B of PTSA salt of TGR-1202 according to any embodiment herein (e.g., a crystalline Form B of PTSA salt of TGR-1202 having a particle size distribution as defined in any embodiment herein). The pharmaceutical composition may include one or more additional active ingredients as described herein.

The excipients may be selected from diluents, fillers, salts, disintegrants, binders, lubricants, glidants, dispersing agents, suspending agents, wetting agents, controlled release matrices, colorants, flavorings, buffers, stabilizers, solubilizers, and combinations thereof.

The pharmaceutical compositions of the present invention can be administered alone or in combination with one or more other active agents. Where desired, the subject compounds and other agent(s) may be mixed into a preparation or both components may be formulated into separate preparations to use them in combination separately or at the same time.

The PTSA salts of TGR-1202 and pharmaceutical compositions described herein can be administered by any route that enables delivery of the TGR-1202 to the site of action, such as orally, bucally, intranasally, topically (e.g., transdermally), intraduodenally, parenterally (including intravenously, intraarterially, intramuscularly, intravascularally, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea).

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

The amount of the PTSA salt of TGR-1202 to be administered is dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. An effective amount of the PTSA salt of TGR-1202 described herein may be administered in either single or multiple doses (e.g., twice or three times a day).

The PTSA salt of TGR-1202 described herein may be used in combination with one or more of anti-cancer agents (e.g., chemotherapeutic agents), therapeutic antibodies, and radiation treatment.

The PTSA salt of TGR-1202 described herein may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs).

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999), all of which are incorporated by reference herein in their entirety.

In one embodiment, the PTSA salt of TGR-1202 described herein is administered at a dose selected to produce a concentration of compound in the blood between about 20 to 5,000 ng/mL, and maintaining such concentration during a period of about 6 to 24 hours following administration. In another particular embodiment, the dose size and frequency are selected to achieve a concentration of compound in the blood that is between about 50 to 2,500 ng/mL and maintain that concentration during a period of about 6 to 24 hours from the time of administration. In some embodiments, the dose size and frequency are selected to achieve a concentration of TGR-1202 in the blood that is between about 100 to 1,500 ng/mL following administration. In some embodiments, the dose size and frequency are selected to achieve a concentration of TGR-1202 in the blood that is between about 100 to 750 ng/mL over a period of about 6 to 24 hours from the time of administration. In further embodiments, the dose size and frequency is selected to achieve a $C_{max}$, plasma level of PTSA salt of TGR-1202 that is at least about 300 ng/mL and does not exceed about 10,000 ng/mL.

Methods of Treatment

The invention also provides methods of using the compounds and pharmaceutical compositions of the present invention to treat disease conditions, including, but not limited to, diseases associated with malfunctioning of one or more types of PI3 kinase.

A detailed description of conditions and disorders mediated by PI3 δ kinase activity is described in, for example, International Publication Nos. WO 2001/81346, WO 2010/123931, WO 2010/0111432 and WO 2010/057048, and in U.S. Publication No. US 2005/043239, each of which is incorporated herein by reference in its entirety for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The invention also relates to a method of treating a hyperproliferative disorder in a subject that comprises administering to said mammal a therapeutically effective amount of a compound of the present invention or a pharmaceutically acceptable salt thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

EXAMPLES

The examples and preparations provided below further illustrate and exemplify the methods of preparing compounds and compositions of the invention. It is to be understood that the scope of the present invention is not limited in any way by the scope of the following examples and preparations.

XPRD patterns were acquired on a X'PertPRO MPD diffractometer equipped with a Cu LFF X-ray tube (45 kV, 40 mA) using the following measurement parameters:

Scan mode: Continuous
PSD mode: Scanning
PSD Length: 2.12 o 2θ
Scan Range: 2.5 to 40 o 2θ
Step size: 0.017/step
Scan Step time: 12.065 s
Divergence Slit type: Automatic
Incident Beam Monochromatic: No
Spinning: Yes

DSC spectra were acquired on a DSCQ2000 V24.11 Build 124.

Example 1: Preparation of the PTSA Salt of TGR-1202 (Form A)

7100 g of TGR-1202 was charged in a reactor containing 56.8 liters of acetone and stirred at ambient temperature. 4680 g of p-toluene sulphonic acid was added and the reaction mixture was heated at a temperature of 60-65° C. for about 6 hours. The solvent was removed by distillation under reduced pressure to obtain a wet residue. The wet residue was degassed and allowed to cool to <20° C. Approximately 142 liters of diethyl ether was then added and the resulting mixture was stirred overnight, then filtered to obtain a solid mass which was washed with diethyl ether and dried in vacuo to yield a solid mass. The solid mass was re-suspended in diethyl ether, stirred for 6 hours, and then filtered to yield a solid mass which was subsequently dissolved in 56.8 liters of acetone, filtered through a HiFlow bed, and concentrated under reduced pressure. The resulting residue mass was stirred with water overnight, then filtered and vacuum dried to yield 6600 g of the PTSA salt of TGR-1202. HPLC: 99.21% and chiral purity of 99.64:0.36 (S:R).

Example 2: Preparation of the PTSA Salt of TGR-1202 (Form B)

1000 g of TGR-1202 was charged in a reactor containing 8 liters of acetone and stirred at ambient temperature. 666 g of p-toluene sulphonic acid was then added and the reaction mixture was heated at a temperature of 60-65° C. for about 6 hours. The solvent was removed by distillation under reduced pressure to obtain a wet residue. The wet residue was degassed and allowed to cool to <20° C. Approximately 20 liters of diethyl ether was added and the resulting mixture was stirred overnight, then filtered to obtain a solid mass which was washed with diethyl ether and dried in vacuo to yield a solid mass which was then vacuum dried to yield 1150 g of the PTSA salt of TGR-1202. HPLC: 99.33% and chiral purity: 99.61:0.39 (S:R).

Table 1 lists the XRPD pattern peaks and relative peak intensities for the products of Examples 1 and 2.

TABLE 1

| Example 1 | | Example 2 | |
|---|---|---|---|
| 2 Theta | Rel. Int. (%) | 2 Theta | Rel. Int. (%) |
| 5.0111 | 90.45 | 5.0368 | 99.91 |
| 6.1947 | 17.54 | 6.2245 | 23.13 |
| 7.3344 | 28.14 | 7.3722 | 27.98 |
| 7.8955 | 23.93 | 7.9120 | 15.31 |
| 8.4677 | 5.77 | 8.4862 | 3.10 |
| 10.0914 | 95.66 | 10.1351 | 100.00 |
| 12.2407 | 38.58 | 12.2720 | 25.41 |
| 13.0311 | 18.40 | 12.4494 | 28.74 |
| 13.3639 | 18.53 | 13.0607 | 18.06 |
| 15.9118 | 43.52 | 13.3947 | 6.18 |
| 16.1260 | 62.05 | 15.9313 | 18.53 |
| 16.3442 | 43.31 | 16.1429 | 30.80 |
| 17.3580 | 33.21 | 16.3476 | 17.15 |
| 17.7652 | 36.83 | 16.7829 | 3.73 |
| 18.1828 | 34.80 | 17.0690 | 9.84 |
| 19.0276 | 20.04 | 17.3057 | 9.38 |
| 19.5461 | 38.96 | 17.4929 | 9.78 |
| 20.0004 | 50.44 | 17.7730 | 16.33 |
| 20.8037 | 38.08 | 18.2136 | 15.19 |
| 21.1204 | 27.38 | 18.4160 | 12.24 |
| 21.7227 | 32.60 | 18.7137 | 6.65 |
| 22.0621 | 78.29 | 19.1252 | 12.24 |
| 22.8416 | 33.03 | 19.6214 | 21.10 |
| 23.1627 | 26.64 | 20.0040 | 25.77 |
| 24.4157 | 100.00 | 20.8028 | 15.49 |
| 25.3391 | 39.04 | 21.1629 | 11.75 |
| 26.9321 | 23.79 | 21.4304 | 8.00 |
| 27.8349 | 14.56 | 21.7505 | 13.89 |
| 28.4163 | 12.04 | 22.1114 | 47.85 |
| 29.2666 | 25.40 | 22.8531 | 9.68 |
| 30.3829 | 10.40 | 23.1912 | 10.23 |
| 34.2390 | 3.40 | 24.4503 | 62.76 |
| 35.8360 | 4.32 | 25.0031 | 15.78 |
| 38.0065 | 6.35 | 25.4128 | 18.58 |
| 38.9170 | 1.78 | 26.6621 | 4.52 |
| | | 26.9692 | 14.35 |
| | | 27.4037 | 4.15 |
| | | 27.8432 | 9.39 |
| | | 28.5253 | 6.78 |
| | | 29.3252 | 17.35 |
| | | 29.6443 | 6.08 |
| | | 30.4781 | 5.95 |
| | | 31.1600 | 1.72 |
| | | 32.5213 | 2.02 |
| | | 32.9371 | 2.57 |
| | | 34.1290 | 1.91 |
| | | 35.6680 | 3.36 |
| | | 36.0502 | 2.33 |
| | | 36.7594 | 2.46 |
| | | 37.1729 | 1.34 |
| (Also see FIG. 1) | | (Also see FIG. 2) | |

Table 1A lists the DSC endotherms for the PTSA salts prepared in Examples 1 and 2.

TABLE 1A

| Example 1 °C. | Example 2 °C. |
|---|---|
| 153.66 | 145.66 |

Example 3: Particle Size Analysis

Particle size (PSD) analysis of the PTSA salts of TGR-1202 prepared in Examples 1 and 2 was performed as described below using a Malvern Master Sizer 2000 with the Scirocco 2000 dry powder system. The instrument parameters were:
Particle RI: 1.50
Absorption index: 0.1
Obscuration range: 1-5%
Analysis Model: General purpose
Sensitivity: Normal
Air Pressure: 2.0 Bar
Feed rate: 30%
Sample measurement Time: 6 Second
Background measurement Time: 6 Second
Number of measurement cycle: 1
Procedure: 5 g of TGR-1202 was transferred into a sample measuring cell (i.e., Scirocco 2000) and the airflow was started. Laser intensity was maintained more than 70%. Measurement was started and the vibration feed rate was increased in order to achieve the obscuration within the limits. Once the obscuration came within the limit, measurement was recorded. Analysis was performed in triplicate and the results provided are an average of three experiments.

The particle size distribution (PSD) for the products of Examples 1 and 2 is shown in Table 2.

TABLE 2

| PTSA salt of TGR-1202 | | | |
|---|---|---|---|
| Example | $d(0.1)$ μm | $d(0.5)$ μm | $d(0.9)$ μm |
| Example 1 | 8.01 | 147.41 | 510.73 |
| Example 2 | 1.07 | 3.98 | 12.18 |

Example 4: Tableting of the PTSA Salts of TGR-1202

Tablet cores containing 200 mg (calculated as free base form) of the PTSA salts of TGR-1202 in Examples 1 and 2 were prepared in order to study their dissolution properties. These formulations are referred to as Examples 4a and 4b, respectively. The particle size distribution for the PTSA salts of TGR-1202 prepared in Examples 1 and 2 is provided in Example 3.

Example 4a

Six different tablets were prepared (T1, T2, T3, T4, T5 and T6) containing the PTSA salt of TGR-1202 prepared in Example 1.

Example 4b

Six different tablets were prepared (T1, T2, T3, T4, T5 and T6) containing the PTSA salt of TGR-1202 prepared in Example 2.
Equipment Used:
The tabletting equipment used is shown in Table 3.

TABLE 3

| Stage | Equipment Name |
|---|---|
| Manufacturing | Sieves 20 or 24#, 40#, and 60# sieve |
| | Rapid Mixer Granulator (RMG) |
| | Stirrer |
| | SS vessels |
| | FBD |
| | Multi Mill with 1.0 mm SS screen |
| | Conta Blender |
| Compression | Compression machine Cadpress |
| | 17.8 × 8.8 mm, oval shaped D-Tooling |
| | Tablet de-dusters |
| | Metal detectors (optional) |

TABLE 3-continued

| Stage | Equipment Name |
|---|---|
| Coating | Coating machine |
|  | Stirrer |
|  | SS vessels |
| Packaging | Heat Induction sealer |

Preparation of Tablets:
The formulations of the tablets are shown in Table 4.

TABLE 4

Formulation 200 mg dose strength (calculated as free base form)

| S. No. | Ingredients | Example 4a | Example 4b |
|---|---|---|---|
| 1 | PTSA salt of TGR-1202 | 260.20 (salt) | 260.20 (salt) |
| 2 | Hydroxypropyl betadex | 270.00 | 270.00 |
| 3 | Microcrystalline cellulose (Avicel PH101) | 41.80 | 41.80 |
| 4 | Croscarmellose Sodium (Ac-Di-Sol) | 20.00 | 20.00 |
| 5 | Hydroxypropyl cellulose (Klucel LF) | 6.00 | 6.00 |
| 6 | Purified Water | q.s | q.s |
| 7 | Croscarmellose Sodium (Ac-Di-Sol) | 70.00 | 70.00 |
| 8 | Magnesium stearate | 2.00 | 2.00 |
|  | Core Tablet Weight | 670.00 | 670.00 |
|  | Coating |  |  |
| 9 | Opadry II Brown 40L565004 | — | 20.10 |
| 10 | Purified Water | — | q.s |
|  | Coated Tablet Weight | — | 690.10 |

Manufacturing Process:
The tablets were prepared as follows:
1. Dispense the raw material quantities as required by the formula.
2. Co-Sift the API with hydroxypropyl betadex, croscarmellose sodium and microcrystalline cellulose through a #40 mesh and collect in an in-process bulk container or double polyethylene bags.
3. Dissolve the weighed quantity of hydroxypropyl cellulose (Klucel LF) in purified water under stirring in a stainless steel container to afford a clear solution (binder solution).
4. Load the blend of step 2 in a rapid mixer granulator (RMG) and mix for 8 minutes at a slow impeller speed with the chopper off.
5. Granulate the blend of step 4 with the binder solution from step 3. Add additional water if required to obtain granules of a suitable consistency. Perform additional kneading if required. Perform intermittent scrapping, when required, during granulation.
6. Dry the wet mass in fluid bed drier (FBD) at an inlet temperature not more than 65° C. until the loss on drying (LOD) is below 3.0% w/w. Perform intermittent scrapping, when required.
7. Pass the dried granules of step 6 through a 24 # sieve and collect the sifted granules separately. Mill 24# retained granules through a Multi mill equipped with a 1.0 mm stainless steel screen at a fast speed with the knives forward. Collect the milled granules and sift through a 24# sieve equipped on a vibratory sifter. Collect the 24# pass granules in a separate polybag.
8. If required, repeat step 7 once again for the 24# retained granules. Collect in the in-process bulk container or double polyethylene bags.
9. Sift croscarmellose sodium through a #40 and mix with the granules of step in a Conta blender at 12 rpm for 8 minutes.
10. Sift magnesium stearate through a #60 mesh and mix with the blend of step 9 in a Conta blender at 12 rpm for 3 minutes.
11. Unload the lubricated granules into double polythene bags. Weigh and record the weight of the lubricated granules.
12. Compress the lubricated blend with 17.8×8.8 mm, oval shape punches with an average weight of 670.00 mg/tab.

The coating procedure described below was performed only for the tablets of Example 4b.

13. Coating Solution preparation: Transfer a weighed quantity of purified water to a container equipped with a mechanical stirrer. Disperse Opadry II Brown 40L565004 in the purified water with continuous stirring and mix for 45 minutes. Filter the resulting suspension through a 100# sieve or nylon cloth.
14. Load the compressed tablets in to a coating pan and continue coating till the required weight gain (2.5-3.5%) is achieved.

The in-process checks (IPC) data for the tablets of Examples 4a and 4b are shown in Tables 5 and 6, respectively.

TABLE 5

Example 4a: IPC data 200 mg strength

| Parameter | Nominal | Average | Range |
|---|---|---|---|
| Weight [mg] | 670.00 ± 5% | 669.70 | 664.8-678.6 |
| Thickness [mm] | — | 5.31 | 5.27-5.35 |
| Hardness [Kp] | 12.0 ± 4.0 | 12.2 | 11.2-13.1 |
| Disintegration [min] | Not More Than 1% |  |  |
| Disintegration [min] | For record only | 14-15 min | |
| Friability | Not More Than 1% | 0.018% | |

TABLE 6

Example 4b: IPC data 200 mg strength

| Parameter | Nominal | Average | Range |
|---|---|---|---|
| Weight [mg] | 670.00 ± 5% | 671.10 | 650-683 |
| Thickness [mm] | — | — | 5.33-5.42 |
| Hardness [Kp] | 12.0 ± 4.0 | — | 12.53-14.83 |
| Disintegration [min] | For record only | 16-17 min | |
| Friability | Not More Than 1% | 0.04% | |

Tablets taken orally remain one of the most effective means of treatment available. The effectiveness of such dosage forms relies on the drug dissolving in the fluids of the gastrointestinal tract prior to absorption into the systemic circulation. The rate of dissolution of the tablet is therefore relevant to its performance.

Dissolution of cores from Examples 4a and 4b was performed using the following parameters: 900 ml of a 0.1N HCl aqueous solution with 1% sodium lauryl sulfate (SLS), paddle apparatus according to USP apparatus 1, paddle speed of 100 rounds per minute, and 6 runs (n=6). The criteria for dissolution in media with a pH of 1 is not less than 75% (Q=75) in 120 minutes. The dissolution results are shown in Table 7 below.

TABLE 7

| Time (min) | Example 4a | | Example 4b | |
| --- | --- | --- | --- | --- |
| | % Drug Release | RSD | % Drug Release | RSD |
| 10 | 24 | 10.1 | 7 | 11.7 |
| 15 | 39 | 8.3 | 15 | 12.4 |
| 30 | 70 | 10.3 | 44 | 8.9 |
| 45 | 78 | 12.3 | 72 | 5.6 |
| 60 | 79 | 13.3 | 91 | 2.3 |
| 90 | 81 | 12.8 | 98 | 2.4 |
| 120 | 82 | 12.1 | 100 | 2.6 |

Example 5

Pharmacokinetics

The oral bioavailability of tablets (Examples 4a and 4b) were evaluated in human healthy volunteers. The protocol for the pharmacokinetics studies is provided below.

All healthy subjects were fasted overnight (12 hours) before dosing and fasting was continued until 4.0 hours after administration of the test formulation. Test formulations (tablets) were prepared as provided in Examples 4a and 4b. Blood samples were collected, and placed into a micro centrifuge tube containing an anticoagulant. The blood samples were centrifuged immediately and separated plasma samples were frozen at below −80° C. and stored until analysis. The plasma concentrations of test items in all samples were analyzed by LC-MS/MS. Pharmacokinetic parameters (i.e., $C_{max}$, $AUC_{0-t}$, $T_{max}$, and $t^{1/2}$) were estimated.

The tablet composition comprising a PTSA salt of TGR-1202 prepared according to Example 2 exhibited a $C_{max}$ about 2.5 fold and an area under the curve (AUC) about 1.9 fold greater than that of the tablet composition comprising a PTSA salt of TGR-1202 prepared according to Example 1. The results are provided in Table 8 below.

TABLE 8

| | Human Pharmacokinetics | |
| --- | --- | --- |
| Parameters | Tablets of Example 4a | Tablets of Example 4b |
| # Healthy Volunteers | 12 | 12 |
| Dose (mg) | 200 | 200 |
| Median $T_{max}$ (hr) | 2 | 3 |
| $C_{max}$ (ng/mL) | 155.97 | 395.49 |
| *$T_{1/2}$ (hr) | 74.92 | 73.59 |
| $AUC_{0-t}$ (µg × hr/mL) | 5.06 | 9.43 |
| $AUC_{0-inf}$ (µg × hr/mL) | 7.28 | 13.92 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent or patent application was specifically and individually indicated to be incorporated herein by reference.

The invention claimed is:

1. A crystalline p-toluenesulfonic acid salt of the compound wherein the crystalline salt exhibits an XRPD pattern having one or more peaks selected from 5.0, 10.1, 22.1, and 24.5±0.2° 2Θ.

2. The salt of claim 1, wherein the salt exhibits an XRPD pattern substantially as shown in FIG. 2.

3. The salt of claim 1, wherein the salt has a d(0.5) of from about 1 to about 10 µm.

4. The salt of claim 1, wherein the salt has a d(0.5) of from about 2 to about 5 µm.

5. The salt of claim 1, wherein the salt has a d(0.9) of from about 5 to about 25 µm.

6. The salt of claim 1, wherein the salt has a d(0.9) of from about 5 to about 15 µm.

7. The salt of claim 1, wherein the salt has a d(0.1) of from about 0.5 to about 1.5 µm.

8. The salt of claim 1, wherein the salt has a d(0.1) of from about 0.5 to about 1.0 µm.

9. The salt of claim 1, wherein the salt is substantially free of other solid state forms of the p-toluenesulfonic acid salt.

10. The salt of claim 1, wherein the salt contains less than 5% of other solid state forms of the p-toluenesulfonic acid salt.

11. A pharmaceutical composition comprising a salt of claim 1 and a pharmaceutically acceptable excipient.

12. A method of inhibiting a catalytic activity of a PI3 δ kinase present in a cell, comprising contacting the cell with an effective amount of a salt of claim 1.

13. The method of claim 12, wherein the inhibition takes place in a subject suffering from a disease or disorder which is cancer, bone disorder, inflammatory disease, immune disease, nervous system disease, metabolic disease, respiratory disease, thrombosis, or cardiac disease.

14. A method for the treatment of a PI3K associated disease or disorder comprising the step of administering to a subject in need thereof an effective amount of a salt of claim 1.

15. The method of claim 14, further comprising the step of administering simultaneously or sequentially to a subject in need thereof at least one other anti-cancer agent, antiinflammatory agent, immunosuppressive agent, steroid, non-steroidal antiinflammatory agent, antihistamine, analgesic, or a mixture thereof.

16. The method of claim 14, wherein the PI3K associated disease, disorder or condition is an immune system-related disease, a disease or disorder involving inflammation, cancer or other proliferative disease, a hepatic disease or disorder, or a renal disease or disorder.

17. The method of claim 14, wherein the PI3K associated disease, disorder or condition is selected from inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis, atopic dermatitis, asthma, Sjogren's syndrome, organ transplant rejection, multiple sclerosis, Guillain-Barre, autoimmune uveitis, autoimmune hemolytic anemia, pernicious anemia, autoimmune thrombocytopenia, temporal arteritis, antiphospholipid syndrome, vasculitides such as Wegener's granulomatosis, Behcet's disease, psoriasis, dermatitis herpetiformis, pemphigus vulgaris, vitiligo, Crohn's disease, colitis, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disorder of the adrenal gland, systemic lupus erythematosus, polymyositis, dermatomyositis, ankylosing spondylitis, transplant rejection, skin graft rejection, arthritis, bone diseases associated with increased bone resorption; ileitis, Barrett's syndrome, adult respiratory distress syndrome, chronic obstructive airway disease; corneal dystrophy, trachoma, onchocerciasis, sympathetic ophthalmitis, endophthalmitis; gingivitis, periodontitis; tuberculosis; leprosy; uremic complications, nephrosis; sclerodermatitis, psoriasis, chronic demyelinating diseases of the nervous system, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immune-complex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma, and cancer.

18. The method of claim 14, wherein the PI3K associated disease, disorder or condition is selected from hematopoietic tumors of lymphoid lineage, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, acute myelogenous leukemias, chronic myelogenous leukemias, myelodysplastic syndrome, promyelocytic leukemia; carcinoma of the bladder, carcinoma of the breast, carcinoma of the colon, carcinoma of the kidney, carcinoma of the liver, carcinoma of the lung, small cell lung cancer, esophageal cancer, gall bladdercancer, ovarian cancer, pancreatic cancer, stomachcancer, cervical cancer, thyroidcancer, prostatecancer, skincancer, squamous cell carcinoma; tumors of mesenchymal origin, fibrosarcoma, rhabdomyosarcoma; tumors of the central and peripheral nervous system, astrocytoma, neuroblastoma, glioma, schwannoma; melanoma, seminoma, teratocarcinoma, osteosarcoma, xenoderoma pigmentosum, keratoctanthoma, thyroid follicular cancer and Kaposi's sarcoma.

19. The method of claim 14, wherein the PI3K associated disease, disorder or condition is selected from chronic obstructive pulmonary disease, asthma, rheumatoid arthritis, chronic bronchitis, atopic dermatitis, multiple sclerosis, inflammatory bowel disease, allergic rhinitis, lupus erythematosus and ulcerative colitis.

20. The method of claim 14, wherein the PI3K associated disease, disorder or condition is selected from hematopoietic tumors of lymphoid lineage, leukemia, acute lymphocytic leukemia, acute lymphoblastic leukemia, B-cell lymphoma, T-cell lymphoma, Hodgkin's lymphoma, non-Hodgkins lymphoma, chronic lymphocytic leukemia, hairy cell lymphoma and Burkett's lymphoma, hematopoietic tumors of myeloid lineage, acute myelogenous leukemias, chronic myelogenous leukemias, myelodysplastic syndrome, promyelocytic leukemia or multiple myelomas which includes smoldering multiple myeloma, nonsecretory myeloma, osteosclerotic myeloma, plasma cell leukemia, solitary plasmacytoma, and extramedullary plasmacytoma.

21. The method of claim 14, wherein the PI3K associated disease, disorder or condition is selected from Chronic Lymphocytic Leukemia (CLL), Lymphoma Non-Hodgkin (NHL), Acute Myeloid Leukemia (AML), Multiple Myeloma (MM), Small Lymphocytic Lymphoma (SLL), Indolent Non-Hodgkin's Lymphoma (I-NHL), acute lymphocytic leukemia (ALL), mantle cell lymphoma (MCL), follicular lymphoma, Waldestrom's macroglobulinemia (WM), T-cell lymphoma, B-cell lymphoma, and diffuse large B-cell lymphoma (DLBCL).

22. A method for the treatment of a relapsed or refractory hematologic malignancy comprising the step of administering to a subject in need thereof an effective amount of a salt of claim 1.

23. The method of claim 22, wherein the malignancy is selected from non-Hodgkin's lymphoma, chronic lymphocytic leukemia, peripheral T-cell lymphoma, and Hodgkin's lymphoma.

24. A method for the treatment of non-Hodgkin's lymphoma, chronic lymphocytic leukemia, peripheral T-cell lymphoma, and Hodgkin's lymphoma comprising the step of administering to a subject in need thereof an effective amount of a salt of claim 1.

25. The salt of claim 1, wherein the salt exhibits a differential scanning calorimeter (DSC) pattern with a characteristic endothermic peak at about 146° C.

26. The salt of claim 1, wherein the crystalline salt exhibits an XRPD pattern having two or more peaks selected from 5.0, 10.1, 22.1, and 24.5±0.2° 2Θ.

27. The salt of claim 1, wherein the crystalline salt exhibits an XRPD pattern having peaks at 5.0, 10.1, 22.1, and 24.5±0.2° 2Θ.

28. The salt of claim 1, wherein the ratio of p-toluene-sulfonic acid to the compound is about 1:1.

* * * * *